United States Patent [19]

Slemeyer

[11] Patent Number: 5,493,891
[45] Date of Patent: Feb. 27, 1996

[54] TEST GAS GENERATOR FOR CALIBRATING GAS METERS

[75] Inventor: Andreas Slemeyer, Marburg, Germany

[73] Assignee: Drägerwerk AG, Lubeck, Germany

[21] Appl. No.: 340,269

[22] Filed: Nov. 15, 1994

[30] Foreign Application Priority Data

Nov. 19, 1993 [DE] Germany .................. 43 39 472.8

[51] Int. Cl.⁶ .................. G01N 37/00; G01N 33/48; B01L 5/00
[52] U.S. Cl. .................. 73/1.00 G; 436/9
[58] Field of Search .................. 73/1 G; 261/124; 436/8, 9

[56] References Cited

U.S. PATENT DOCUMENTS

| | | | |
|---|---|---|---|
| 3,614,855 | 10/1971 | Van Luik, Jr. | 73/1 G |
| 3,760,773 | 9/1973 | Christensen | 73/1 G |
| 3,885,414 | 5/1975 | Reville | 73/1 G |
| 3,890,100 | 6/1975 | Busch | 436/9 |
| 4,003,240 | 1/1977 | Durbin | 73/1 G |
| 4,069,701 | 1/1978 | Baldauf et al. | 73/1 G |
| 4,351,743 | 9/1982 | Hashimoto | 436/9 |
| 4,407,152 | 10/1983 | Guth | 73/1 G |
| 4,474,048 | 10/1984 | Schmidt | 73/1 G |
| 4,625,543 | 12/1986 | Ertl et al. | 73/1 G |
| 4,723,436 | 2/1988 | Moreth et al. | 73/1 G |
| 4,793,173 | 12/1988 | Moreth et al. | 73/1 G |

FOREIGN PATENT DOCUMENTS

| | | | |
|---|---|---|---|
| 1491190 | 11/1977 | Germany | 73/1 G |
| 2804288 | 8/1979 | Germany | 73/1 G |
| 3216109 | 11/1983 | Germany . | |
| 7579 | 4/1979 | Japan | 436/9 |

*Primary Examiner*—Hezron E. Williams
*Assistant Examiner*—Daniel S. Larkin
*Attorney, Agent, or Firm*—McGlew and Tuttle

[57] ABSTRACT

A device for generating a test gas e.g., ethanol has at least two series-connected containers, which are filled with a calibration solution. A carrier gas, which is enriched with the calibration substance present in the solution corresponding to the vapor pressure of the calibration substance at the given temperature, is passed through these calibration containers. To prevent or to reduce the depletion of the components necessary for the gaseous calibration substance in the calibration solution, a defined amount of a stock solution is fed through the calibration containers in counterflow to the direction of delivery of the carrier gas.

18 Claims, 2 Drawing Sheets

TEST GAS GENERATOR FOR CALIBRATING GAS METERS

FIELD OF THE INVENTION

The present invention pertains to a device for generating a test gas with a predetermined content of a gas component to be detected by a meter. The device includes at least two containers, which are connected in series, through which a carrier gas flows, and each of which contains an aqueous solution of a liquid, which occurs in the gaseous state at an equilibrium concentration that becomes established above the liquid level, and which mixes with the carrier gas.

BACKGROUND OF THE INVENTION

Such a device has become known from German Offenlegungsschrift No. DE-OS 32,16,109. The prior-art test gas generator is used to generate a test gas mixture of defined composition by evaporating a substance contained in an aqueous solvent, ethanol in the prior-art gas generator, and which is at equilibrium with the gas phase, in which a corresponding ethanol concentration will then be present. A carrier gas, e.g., ambient air, is pumped through the liquid by means of a frit via a delivery means, so that the carrier gas becomes enriched with ethanol. In addition, a corresponding portion of the gaseous test gas present in the liquid is expelled from the container. The distribution ratio of the concentration in the gas phase above the solution to that in the liquid phase is described by Henry's constant k. Since this constant is temperature-dependent, thermostatting of the solution is provided. The test gas being expelled from the solution container is fed as a new carrier gas into a second solution container, which is arranged, in terms of flow, downstream of the first one. The ethanol-enriched carrier gas which is delivered from the first solution container is again bubbled through the solution in the second solution container as well, and it is expelled from the second solution container. Due to this cascading through two solution containers, the carrier gas flowing through is already extensively enriched with the calibrating substance (ethanol in the prior-art case) in the first container. If this enriched carrier gas flows through the second solution container, only a small amount of calibrating substance needs to be taken up in that container to completely saturate the carrier gas with the calibrating substance. The depletion of the calibrating substance in the second solution container is consequently far less than in the first one. When the concentration of the calibrating substance to be detected in the first solution container has decreased by the end of the usable life of the prior-art generator to the extent that it would no longer be suitable for calibration purposes, sufficient enrichment of the carrier gas with the calibrating substance to be detected still takes place in the next solution container. If the solution containers are assumed to be, e.g., wash bottles containing 0.5 L of an ethanol solution with an ethanol concentration of 1‰, a 0.5% deviation of the test gas concentration from the initial value will become noticeable upon the cumulative flowthrough of a carrier gas volume of ca. 40 L. Even though it would be possible to increase the cascading of the solution containers by adding a third solution container or even more solution containers, this would lead to an undesirable increase in the space requirement and the weight of such a test gas generator. In addition, the gas concentration generated would not remain constant over the long term, either.

SUMMARY AND OBJECTS OF THE INVENTION

The basic object of the present invention is to improve a test gas generator of the class described such that the number of possible calibrations, and consequently the usable life of the calibrating solution, are increased, and the stability of the calibrating concentration generated is improved.

This object is attained by a delivery line from a reservoir filled with a stock solution opening into the solution containers for renewing the used solution, and by a delivery means filling these solution containers with the stock solution one after another opposite the direction of flow of the carrier gas, removing the amount of stock solution fed in and feeding it to the next solution container, and emptying the excess of stock solution replenished into a collection tank at the end of the delivery line.

The advantage of the present invention is essentially the fact that the losses of the amounts of calibration substance present in the solution, which are caused by evaporation, are compensated by feeding in a fresh stock solution from a reservoir. It is achieved due to the arrangement of the carrier gas flow and the direction of delivery of the stock solution in counterflow that the still least depleted solution is first renewed in the last solution container, and this renewed solution is filled into the solution container preceding the solution container that is the last container in terms of flow, because this solution container contains an already more extensively depleted concentration in the solution, so that this solution can be improved more effectively. If the stock solution were filled into the solution containers arranged in a cascade pattern in the same direction as the carrier gas, the fresh stock solution would flow into the most depleted solution of the solution container, the solvent that has not yet been completely renewed would also be filled from the first container into the second one, and it would bring about an undesired depletion of the concentration of the test gas substance present in it. Due to the arrangement of the carrier gas flow and the direction of deliver of the stock solution according to the counterflow principle, the more highly concentrated solution of the solution container, which is the last solution container in,the direction of flow of the carrier gas, is thus introduced into the more extensively depleted solution of the solution container that precedes it in terms of flow, rather than introducing the more extensively depleted solution into the more highly concentrated solution of the corresponding solution container, as it would happen in the case of parallel flow of the carrier gas and the stock solution.

The device according to the present invention may be used, in principle, for all the gases used for the purpose of calibrating gas sensors and gas meters, which can preferably be dissolved in a solvent and can be introduced into a gas phase. Calibrating gases which require the presence of water vapor during practical use are especially suitable for use as such calibrating gases. These include, e.g., ethanol solutions for calibrating meters for determining the alcohol in breath. These are especially suitable because one has always been faced with the difficulty that gaseous alcohol is unstable and condenses or dissolves in the water vapor present. The gaseous alcohol is no longer available in the gaseous state when the container with the calibrating gas is stored or even used for a relatively long time. The prior-art wash bottles, which contain a defined amount of an ethanol solution of a defined concentration, through which a carrier gas bubbles, are therefore usually used to generate the calibrating gas concentration. However, since such test gas generators are expensive and heavy, it is necessary to extend their service life as much as possible within intended accuracy limits precisely for the purpose of calibrating meters or determining the alcohol concentration in breath.

Since the equilibrium between the gas phase and the liquid phase of the calibrating substance generated by the test gas generator depends on the temperature of the solvent, it is advantageous to accommodate at least the solution containers and possibly also the carrier gas line and the delivery line in a thermostatted housing.

It is particularly advantageous to form the delivery means from a plurality of hose pumps, each of which delivers the stock solution separately into one container, again removes it from that container, delivers it into the next container, and finally empties it into the collection tank. Thus, a separate hose pump is associated with each solution container, and since this hose pump operates as a regenerative pump, it again removes the amount of stock solution fed in, mixed with the solution originally contained in the solution container, depending on the filling level of the solution container, and delivers it into the next solution container. It is thus unnecessary to impose such strict requirements in terms of accuracy on the capacity of the pump in question. If the first pump delivers more stock solution into the solution container than the next pump is able to remove, only the capacity of the next pump needs to be increased, so that overflow of the solution container is avoided. If it is ensured that the pump that is the last one when viewed in the direction of delivery has the highest pump capacity and the first pump has the lowest pump capacity of all pumps, it is always guaranteed that no more stock solution is fed in than can be removed. If hose pumps are used, the additional advantage is achieved that no gas can escape into the reservoir or the collection tank even at excess pressures of a few bar in the wash bottles.

The component to be detected, which is dissolved in the solution, is depleted as a consequence of the flow of the carrier gas through the solution containers. For example, the ethanol content in the solution continuously decreases in the course of use. In order for the solution to always contain the required ethanol concentration, the ethanol concentration in the solution container is again renewed or refreshed. If this is done in excess, one can be certain that the concentration will not decrease in the solution container. A compensation factor $k_1$ can be defined from the ratio of the amount of fed-in calibration substance to be detected (ethanol in this example) to the amount of calibration substance lost due to evaporation. A compensation factor of, e.g., $k_1=5$ means that the amount of alcohol fed in from the stock solution is 5 times the amount that was removed from the solution due to evaporation as a result of the carrier gas being passed through the solution container. The amount of stock solution to be delivered, $V_{fl}$, which must be passed consecutively through the solution containers by the delivery means, can then be determined from the following equation $$V_{fl} = V_G \cdot k_1 \cdot k.$$

Here, k is the so-called Henry constant, which describes the distribution ratio of, e.g., the ethanol concentration in the gas phase and the liquid phase (the value of k is, e.g., ½500 at 34° C. for ethanol), $V_G$ is the amount of carrier gas having flown through (measured with a gas volume meter), and $k_1$ is the ratio of the gas component to be detected that was fed in to the gas component to be detected that was consumed in the solution due to evaporation (so-called compensation factor). Thus, it is necessary to feed in 8 mL of stock solution from the reservoir in the case of a calibration solution for ethanol at $k=\frac{1}{2500}$ and with a compensation factor of $k_1=20$, and a carrier gas volume of 1 L.

Using the test gas generator described, it is possible to maintain the concentration of the calibration gas mixture generated within very narrow error limits even over rather long service lives. The deviation of the actual concentration from the concentration once generated within the calibration solution can be maintained at <0.3% in the numerical examples described. In most cases, this is sufficient for the calibration possibility of gas meters that meets the current requirements. The deviation can be further reduced by selecting a high compensation factor.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DETAILED DESCRIPTION OF THE PREFERRED EMBODIMENT

Figure 1:
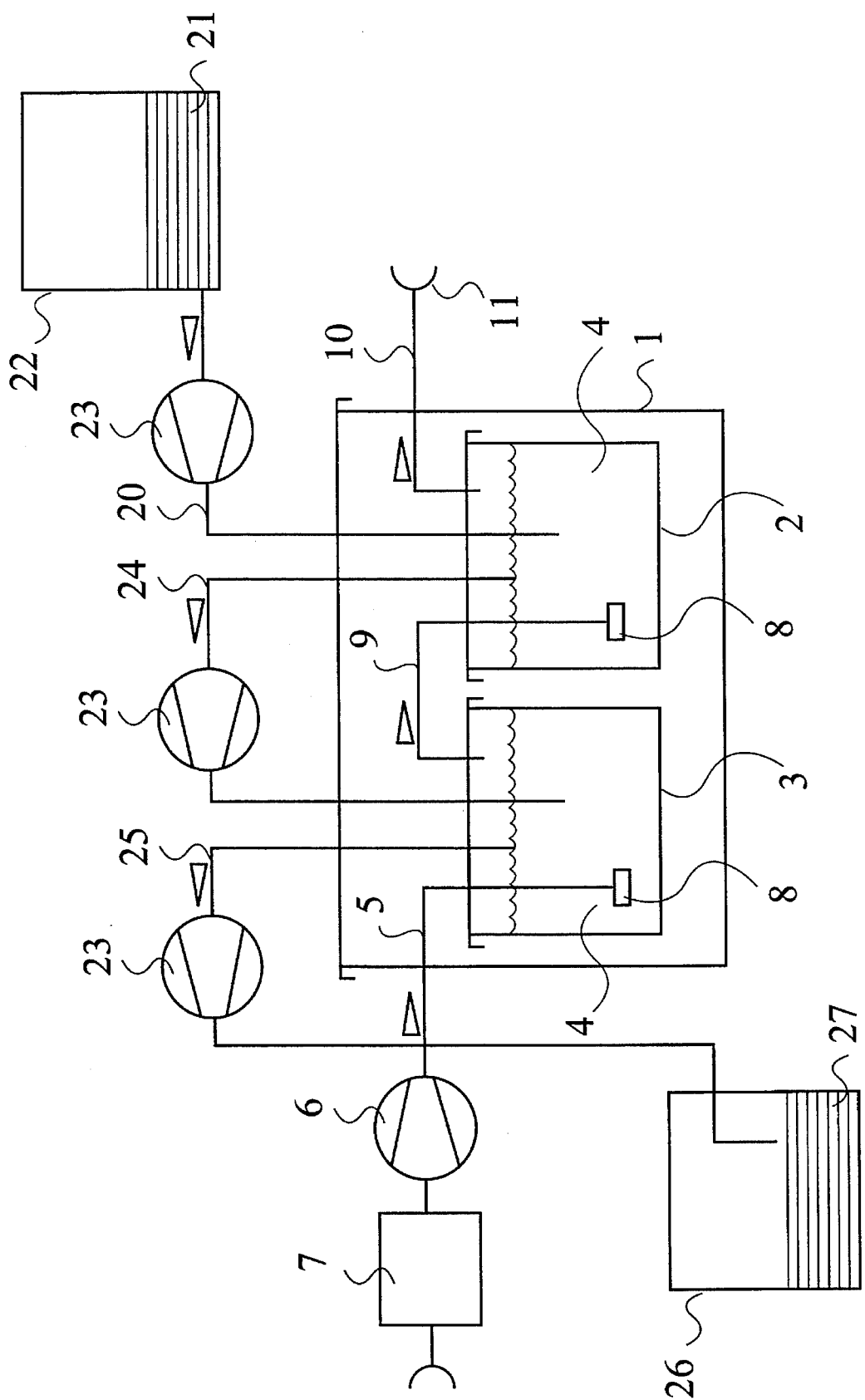
FIG. 1 is a block diagram of a test gas generator.

The block diagram according to FIG. 1 shows the test gas generator in its assembly in a thermostatted housing 1, which accommodates two solution containers 2, 3, which are filled with a calibration solution 4 of predetermined ethanol concentration, here C=1‰. Ambient air is bubbled through the solution containers 2, 3 by a carrier gas pump 6 via a carrier gas line 5. The carrier gas pump 6 draws in ambient air via a volume meter 7. The carrier gas line 5 opens into the first solution container 3 in a frit 8, as a result of which the carrier gas bubbles into the calibration solution 4. A transfer line 9, which opens, via a frit 8, into the calibration solution 4 of the solution container 2 following it, is arranged in the gas phase located above the calibration solution 4. The carrier gas is released from the solution container 2 to a calibration pipe connection 11 via an outlet line 10. During its passage from the carrier gas line to the calibration pipe connection 11, the ambient air is enriched with a calibration gas ethanol concentration that becomes established within the housing due to the Henry constant k of the calibration solution 4 at a given temperature. The calibration pipe connection 11 is connected to a gas sensor or a gas analyzer not shown. A delivery line 20 for a stock solution 21, which is in a reservoir 22, extends opposite the direction of flow of the carrier gas from the volume meter 7 to the calibration pipe connection 11. The delivery line 20 delivers an amount of stock solution 21 metered by a delivery pump 23 into the calibration solution 4 of the second solution container 2. A transfer line 24 with a delivery pump 23 belonging to it draws a corresponding amount of calibration solution 4 from the solution container 2 into the calibration solution 4 of the solution container 3. Finally, the delivery pump 23 in a drain line 25 frees the solution container 3 from the amount of calibration solution which was delivered by the pump 23 from the solution container 2 into the solution container 3. The drain line 25 ends in a collection tank 26, which contains the calibration solution 4 replaced from the solution containers 2, 3 as a residual solution 27. The delivery pumps 23 may be individual pumps, as is shown, but they may also be formed by a single hose pump, which has a triple delivery head, in which the delivery line 20, the transfer line 24, and the drain line 25 with correspondingly different hose diameters are accommodated. The carrier gas pump 6 may be a reciprocating pump.

Figure 2:
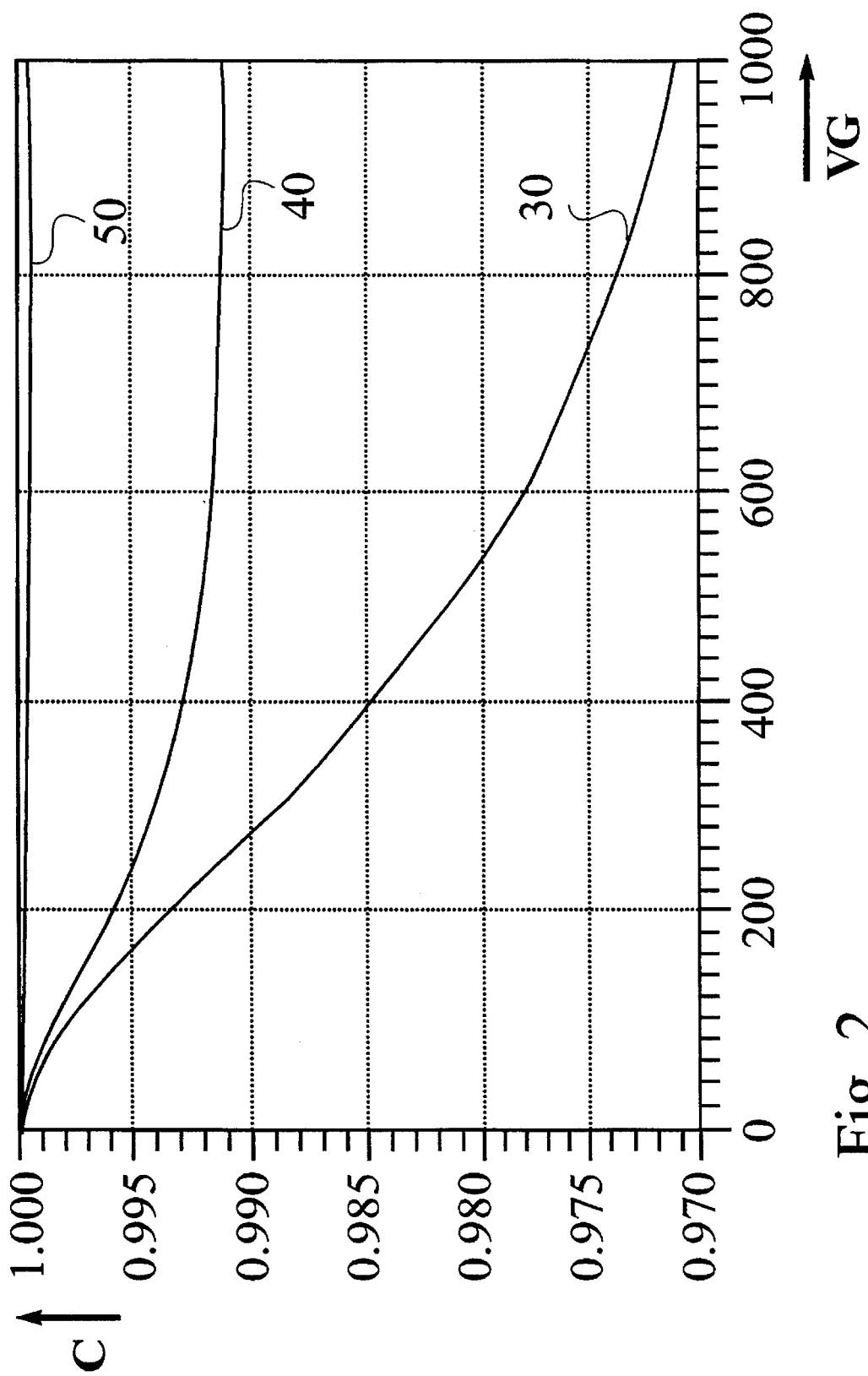
FIG. 2 is a diagram showing the changes in the solvent concentration generated as a function of the amount of carrier gas at different compensation factors $k_1$.

FIG. 2 shows the changes in the ethanol concentration in the calibration solution 4 of the solution containers 2, 3 as a function of the total amount of carrier gas fed through the calibration solutions 4. The concentration values C, standardized to 1, are shown on the ordinate. The abscissa shows the amount of carrier, gas $V_G$ delivered between 0 and 1,000 L. FIG. 2 shows three different curves 30, 40, 50. The parameter for the curves 30, 40, 50 is the compensation factor $k_1$, which is $k_1=5$ for curve 30, $k_1=10$ for curve 40, and $k_1=50$ for curve 50. It is seen at the compensation factor of $k_1=5$ that only 3% of the value of the initial concentration has been removed from the calibration solution 4 after 1,000 L of carrier gas was fed through the calibration solution 4. The rest was always filled up by the stock solution 21. A drop in concentration by less than 1% is obtained for the middle curve 40 at $k_1=10$ after the passage of 1,000 L of carrier gas. Finally, at a compensation factor of $k_1=50$, the deviation of the actual concentration in the calibration solution 4 from the original value can no longer be observed. The accuracy of the concentration at the compensation factor of $k_1=5$ is sufficient in most cases, which is facilitated especially by the fact that this requires the consumption of only a small amount of stock solution 21.

FIG. 2 also shows that the concentration curves tend toward a corresponding asymptotic limit value, and that the higher the compensation factor selected, the sooner is this limit value reached, and the smaller is the deviation of this limit value from the initial concentration.

While a specific embodiment of the invention has been shown and described in detail to illustrate the application of the principles of the invention, it will be understood that the invention may be embodied otherwise without departing from such principles.

What is claimed is:

1. Device for generating a test gas with a pre-determined content of a gas component to be detected by a meter, comprising: at least two containers; gas flow means for connecting said containers in series for flow of a carrier gas therethrough, said carrier gas having a direction of flow, each of said containers containing an aqueous calibration solution of a liquid, which occurs in a gaseous state at an equilibrium concentration, said gaseous state being established above a liquid level of each of said containers and mixing with said carrier gas; a reservoir filled with a stock solution; delivery line means opening into said containers for filling said containers with said stock solution, one after another, in a direction opposite said direction of flow of said carrier gas and further for removing an amount of said stock solution and feeding said amount to a subsequent solution container, in said direction opposite said direction of flow of said carrier gas and for draining an excess of stock solution into a collection tank at an end of said delivery line means.

2. Device according to claim 1, wherein said solution is an aqueous ethanol solution.

3. Device according to claim 1, wherein at least one of said solution containers or one of said solution containers and said carrier gas line and said delivery line means are accommodated in a thermostat regulated housing.

4. Device according to claim 2, wherein at least one of said solution containers or one of said solution containers and said carrier gas line and said delivery line means are accommodated in a thermostat regulated housing.

5. Device according to claim 1, wherein said delivery line means includes a plurality of hose pumps for delivery of said stock solution into said solution containers and for removing said stock solution from said containers for feeding said stock solution to a subsequent container and for finally emptying solution into a collection tank.

6. Device according to claim 2, wherein said delivery line means includes a plurality of hose pumps for delivery of said stock solution into said solution containers and for removing said stock solution from said containers for feeding said stock solution to a subsequent container and for finally emptying solution into a collection tank.

7. Device according to claim 3, wherein said delivery line means includes a plurality of hose pumps for delivery of said stock solution into said solution containers and for removing said stock solution from said containers for feeding said stock solution to a subsequent container and for finally emptying solution into a collection tank.

8. Device according to claim 4, wherein said delivery line means includes a plurality of hose pumps for delivery of said stock solution into said solution containers and for removing said stock solution from said containers for feeding said stock solution to a subsequent container and for finally emptying solution into a collection tank.

9. Device according to claim 1, wherein said delivery line means has a capacity for delivering stock solution which is set at a determinable ratio with respect to a carrier gas volume delivery.

10. Device according to claim 2, wherein said delivery line means has a capacity for delivering stock solution which is set at a determinable ratio with respect to a carrier gas volume delivery.

11. Device according to claim 8, wherein an amount of stock solution $V_{fl}$ to be delivered by said delivery means is determined by an equation $V_{fl}=V_g \cdot k_1 \cdot k$, wherein $V_g$ is the amount of the carrier gas, k is the distribution ratio of the gas component to be detected in the calibration solution, and $k_1$ is the ratio of gas component to be detected, which is fed in, to the gas component consumed by evaporation in the calibration solution.

12. Device according to claim 11, wherein k equals 1/2,500 for ethanol.

13. Device for generating a test gas with a predetermined content of a gas component to be detected by a meter, comprising: a first container; a second container; carrier gas flow means connecting said first container and second container in series, each of said first container and second container containing an aqueous calibration solution of a liquid, said solution occurring in a gaseous state at an equilibrium concentration, said solution in a gaseous state being established above a liquid level of said first container and being established above a liquid layer of said second container, said carrier gas flow means delivering carrier gas first to said first container and subsequently to said second container, to provide a carrier gas flow direction; a reservoir filled with a stock solution; delivery line means connected to said reservoir for delivering said stock solution to said first container and said second container, said delivery line means filling said second container with said stock solution and removing stock solution from said second container and feeding stock solution removed to said first container and draining excess stock solution from said first container to move stock solution in a direction opposite to said carrier gas flow direction; and a collection tank for receiving stock solution removed from said first container.

14. Device according to claim 13, wherein said solution is an aqueous ethanol solution.

15. Device according to claim 13, wherein at least one of said solution containers or one of said solution containers and said carrier gas line and said delivery line means are accommodated in a thermostat regulated housing.

16. Device according to claim 13, wherein said delivery line means includes a plurality of hose pumps for delivery of a stock solution into said solution containers and for removing stock solution from said containers for feeding solution to a subsequent container and for finally emptying solution into a collection tank.

17. Device according to claim 13, wherein said delivery line means has a capacity for delivering stock solution which is set at a determinable ratio with respect to a carrier gas volume delivery.

18. Device according to claim 17, wherein an amount of stock solution $V_{fl}$ to be delivered by said delivery line means is determined by an equation $V_{fl}=V_g \cdot k_1 \cdot k$, wherein $V_g$ is the amount of the carrier gas, k is the distribution ratio of the gas component to be detected in the calibration solution, and $k_1$ is the ratio of gas component to be detected, which is fed in, to the gas component consumed by evaporation in the calibration solution.

* * * * *